United States Patent [19]
Wright

[11] Patent Number: 6,048,205
[45] Date of Patent: Apr. 11, 2000

[54] BIOCOMPATIBLE DENTAL RESTORATION SYSTEM USING LAYERS OF HIGH STRENGTH CERAMIC, GOLD, AND PORCELAIN

[76] Inventor: Cynthia K. Wright, 27 Timberwick, Santa Fe, N.Mex. 87505

[21] Appl. No.: 09/267,331

[22] Filed: Mar. 12, 1999

Related U.S. Application Data

[60] Provisional application No. 60/077,735, Mar. 12, 1998.

[51] Int. Cl.$^7$ .............................. A61C 13/00; A61C 13/08
[52] U.S. Cl. ....................................... 433/202.1; 433/200.1
[58] Field of Search .............................. 433/202.1, 200.1, 433/223

[56] References Cited

U.S. PATENT DOCUMENTS

| | | | |
|---|---|---|---|
| 4,585,417 | 4/1986 | Sozio et al. ........................... | 433/202.1 |
| 4,681,633 | 7/1987 | Watanabe et al. ................ | 433/202.1 X |
| 4,806,383 | 2/1989 | Poltz ................................ | 433/202.1 X |
| 5,288,232 | 2/1994 | Panzera et al. ................... | 433/202.1 X |
| 5,447,967 | 9/1995 | Tyszblat ............................ | 433/202.1 X |

OTHER PUBLICATIONS

*All–Ceramic Restorations with the In–Ceram System*, a short manual by A. Huls, Gottingen, Feb. 1995.
A Renaissance of Ceramic Prothestics? Quintessence of Dental Technology, Norbert Futterknecht and Vanik Jinoian, Quintessence Publishing Co., 1992.

Gramm Technology, Inc., "Telegramm" Newsletter, Jan., 1998.

*Primary Examiner*—Nicholas D. Lucchesi
*Attorney, Agent, or Firm*—Kevin Lynn Wildenstein

[57] ABSTRACT

The present invention is a multilayer dental system for the production of restorations which incorporates a high strength bridging ceramic core, a layer of biocompatible metal for aesthetics and encasing the abutment and a conventional porcelain top layer. The restoration is made by producing the high strength bridging ceramic core, electroforming the 24 K gold upon the core, and then completing the restoration by applying outer layers of conventional dental porcelain. A restoration of the present invention has a natural appearance, is lightweight, is highly biocompatible, does not impart thermal sensitivity, and is strong enough to be used for posterior bridgework. The system of the present invention eliminates the use of toxic alloys and will not result in unsightly oxidation, as is seen with other cast metal restorations. The high strength ceramic core does not slump with repeated firings the way cast alloys do when fired. The completed units can be bonded or cemented within the patient's mouth, and are easily handled by the dentist.

18 Claims, No Drawings

BIOCOMPATIBLE DENTAL RESTORATION SYSTEM USING LAYERS OF HIGH STRENGTH CERAMIC, GOLD, AND PORCELAIN

This application claims benefit of provisional application No. 60/077,735 filed Mar. 12, 1998.

FIELD OF THE INVENTION

This invention relates to a system for producing biocompatible restorations using layers of high strength ceramic, gold or other biocompatible metal, and porcelain, and the restorations, or other objects, thus produced.

BACKGROUND OF THE INVENTION

Electroforming is the electrolytic deposition of dimensionally stable metal layers on a substrate. Invented in 1838 by Jacobi in Russia, this technique was adapted for use in dentistry in 1856 by Newell. The use of this technique in dentistry was greatly expanded by the work of O. W. Rogers, who patented an apparatus and method of electroforming dental crowns in U.S. Pat. No. 4,288,298. The development of nontoxic plating solutions having high penetration power made it possible to produce porcelain fused to gold dental restorations where the gold deposition is of a precise and uniform thickness. This application was limited to a single crown, however, until the development of the cast metal pontic technique for bridges, and the 24 K gold was electroformed over the metal and abutments. The result was a multilayer metal bridge having sufficient stability for multiple units, that is, a bridge which spans multiple teeth. Two articles which discuss the use of electroforming in this way are "Electroforming as an Alternative to Full Ceramic Restorations and Cast Substructures" by Ronald M. Stewart, published in Trends and Techniques in the Contemporary Dental Laboratory, April 1994:42–47 and "Electroforming Technology for Ceramometal Restorations" by Tonino Traini, published in Quintessence of Dental Technology, 1995: 21–28. Gramm Technology, of Woodbridge, Va. and Tiefenbronn, Germany both manufacture dental systems for electroforming gold and related products. The founder of Gramm Technology, Gerhard Gramm, has several U.S. and foreign patents in this area, including U.S. Pat. No. 5,173,161, which describes a device for electroforming work pieces and WO 9207977, which describes a device for coating workpieces used in the dental field.

Electroformation is also used in dentistry as a casting method to produce accurate dental prostheses, as described in U.S. Pat. No. 5,316,650, to Ratzker et al. This technique uses a metallic glass alloy containing cobalt and phosphorus. U.S. Pat. No. 4,451,639, to Prasad describes special metallic ceramics which have been developed for use in the electroforming process. The ceramic of Prasad contains many metals, including palladium, cobalt, gallium, gold, aluminum, copper, zinc and ruthenium or rhenium. Additionally, electroforming is used in other manufacturing methods beyond dentistry. For example, U.S. Pat. No. 5,393,405, to Iacono et al., discusses the production of jewelry using electroformation of multiple layers of gold where the layers differ in hardness.

Ceramic restorations have long been an alternative to metal structures, having vastly superior aesthetics and perfect biocompatibility. Developments in high strength ceramics, that is, ceramics having a flexural strength greater than 300 megapascals (MPa), have made all-ceramic bridges possible. Such high strength ceramic is necessary for producing the coping portion of the all-ceramic restoration. In particular, as described in U.S. Pat. No. 5,695,337 to Sadoun, a ceramic formulation containing multiple metal oxides displays the desired strength. The amount of $Al_2O_3$ has been increased to 85% by weight in a commercial product known as In-Ceram, produced by VITA Zahnfabrik H. Rauter GmbH & Co., Bad Sackingen, Germany. This ceramic has a strength of 600 MPa and functions well in single units and anterior bridges. The general method of using this material is reported in "Working with the In-Ceram Porcelain System" by Harry Levy and Xavier Daniel, published in Prothése Dentaire 44–45 45: June–July 1990. A further discussion of this technique can be found in "A renaissance of ceramic prosthetics?" by Norbert Futterknecht and Vanik Jinoian, published in Quintessence of Dental Technology, special reprint, 1992. The inceram zirconia high strength ceramic ($AL_2O_3$—$ZrO_2$) has considerably improved mechanical characteristics. This makes posterior bridges possible. Due to the increased opacity, however, there are aesthetic limitations.

Each of these dental systems have serious drawbacks. Metal-base restorations have biocompatibility problems, often reflected as gingival degeneration, which reveals a dark metal margin on the restored tooth which ruins the aesthetic appearance of the restoration. Metal has poor thermal conductivity qualities and can corrode over time. The preparation of metal copings often involves toxic metals which present environmental problems for the dental office personnel and during disposal. Ceramic restorations, when of sufficient strength for posterior bridgework, are too opaque to provide good aesthetics. The present invention has solved these problems by providing a restoration which does not contain materials which cause reactions in the body, do not promote temperature sensitivity, and are relatively non-toxic. Additionally, the present invention provides vivid aesthetics with the warm color of the 24 K gold deposition, and of all the alloys, 24 K gold is highly biocompatible.

SUMMARY OF THE INVENTION

Accordingly, the present invention is a multilayer dental system for the production of restorations which incorporates a high strength bridging ceramic core, a layer of 24 K gold for aesthetics, and a conventional porcelain top layer. The restoration is made by producing the high strength bridging ceramic core, electroforming the 24 K gold upon the core and abutments, and then completing the restoration by applying outer layers of conventional dental porcelain. A restoration employing the present invention has a natural appearance, is lightweight, is highly biocompatible, does not impart thermal sensitivity, and is strong enough to be used for posterior bridgework. The system of the present invention eliminates the use of toxic alloys and will not result in unsightly oxidation, as is seen with other cast metal restorations. The high strength ceramic core does not slump with repeated firings the way cast alloys do when fired. The completed units can be bonded or cemented within the patient's mouth, and are easily handled by the dentist.

DETAILED DESCRIPTION OF THE INVENTION

The present invention is a multilayer dental system that can be used to produce restorations that have excellent aesthetics and are biocompatible. A preferred embodiment of the system utilizes three layers. The bridging core of the system is high strength ceramic, preferably a ceramic high in aluminum oxide or zirconia content. The second layer a biocompatible metal, preferably 24 K gold, which is electroformed onto the high strength bridging ceramic core and abutments after application of a bonder to the ceramic core. Those of skill in the art will realize that the biocompatible metal may include platinum. The final layer is one or more applications of conventional dental porcelain, which are baked onto the metal surface after a second application of bonder to the surface of the electroformed metal. Thus, the bonder is used both to attach the core ceramic to the metal and the metal to the outer porcelain layer. Once all three layers are present, the restoration undergoes a final contour stain and/or glaze to achieve the desired appearance, and is then ready for the dentist to cement or bond the restoration in the patient's mouth.

In order to produce the high strength bridging ceramic core for the system of the present invention, an impression and a master cast are produced in the manner well known in the art. For example, the impression can be taken using the putty/wash technique or any non shrink silicone material or reversible hydrocolloid. Whatever method is used, the impression should be clean without air bubbles, free from distortion, and the margins of the prepared tooth should be visible in the impression. The impression is used to produce the master cast using standard techniques and duplicate models are produced from the master. Specifically, once the master cast dies have been sectioned, the margins are exposed and marked with a pencil. The undercuts should be blocked out with wax, particularly if a bridge abutment is being produced. If the model is cast in stone, two coats of dies spacer should be applied. Epoxy resin models require three coats. The die spacer should be easily removable and should remain on the die only during duplication.

An impression of the sectioned dies of the master are taken with high quality silicone. Optec-Exact (Generic Pentron, Wallingford, Conn.) or Elite vinyl polysiloxane (Zhermack, Rovigo, Italy) are suitable for this purpose. This impression is then cast with plaster specific for this use, In-Ceram plaster, produced by VITA, Bád Sackingen, Germany. The plaster must be mixed according to an exact water to powder ratio to insure that the core will be the correct size after sintering. Once the stone has hardened fully, the cast is removed from the impression, the margins are marked with pencil, and a sealer is applied to the entire cast.

The next step in the process is preparation of the $Al_2O_3$ or $Al_2O_3$—$ZrO_2$ slip. Mixing fluid is combined with a small amount of binder, i.e. one drop binder to 5 ml mixing fluid. This mixture is placed in an ultrasonic unit, and the $Al_2O_3$ powder—38 g for 5 ml of slip—is sprinkled into it. The mixing and ultrasonic unit transforms the paste into liquid slip, similar in consistency to oil paint. The slip is placed under vacuum for several seconds before use. Slip can be applied using a brush with synthetic bristles, or by dipping. Once the cast has been built up with the slip, the margins should be reduced with a scalpel-like instrument until the previously placed pencil line is visible. This shaping process is not difficult, because the slip is similar to wax in consistency and feel.

The built up cast with the slip is then fired two times, but can be fired at least once. During the first firing, the temperature is slowly raised from 20° C. to 120° C. over 6 hours. During this time, the stone gives off moisture and shrinks away from the core. The firing temperature is then raised from 120° C. to 1120° C. at a rate of 10° C. per minute and this temperature is held for 2 hours. This firing results in a solid phase sintering, where the $Al_2O_3$ crystals fuse. The core is removed from the cast and transferred to the master dies in order to check the precision of the fit. Adjustments to the fit of the core can be made using a diamond burr.

The final step in the production of the high strength bridging ceramic core is a glass filtration firing. The infiltration of glass provides the strength to the core. The glass powder is mixed with water and a thick coating is applied to the core, which is placed on a piece of platinum foil. The core is then fired where the temperature is raised quickly to 1100° C., where it remains for a time dependent on the thickness of the core wall. During this time the glass liquefies and infiltrates the $Al_2O_3$ or $Al_2O_3$—$ZrO_2$ of the core. Once the firing is complete, a sandblaster can be used to remove the excess glass. For example, the sandblaster can be loaded with 50 micron $Al_2O_3$ and run at a pressure of 6 $kg/cm^2$ or 80 $lb/in^2$.

The completed high strength bridging ceramic core is then brushed over with a bonder, preferably Bonder A, produced by Gramm Technology, of Woodbridge, Va. and Tiefenbronn, Germany. Bonder is put on the core wherever metal deposition is desired. Generally, the entire outer surface of the restoration requires a layer of metal, and the inner surface, that is, the surface ultimately in contact with the patient's prepped teeth is not coated. Partial coverage is also possible, where only a pontic is created with approximal rests. The bonder is fused to the core by baking in an oven at 950° C. for approximately six minutes. A stone duplicate is glued to the core, and a copper wire is attached to the duplicate by drilling a small hole and gluing the tip of the wire to the stone with cyanoacrylate glue. Silver lacquer is also applied to complete the electrical path between abutments and the bonder on the ceramic core and the wire. Standard electroforming equipment, such as the Gammat Dent, produced by Gramm Technology, of Woodbridge, Va. and Tiefenbronn, Germany is used to electroform the metal onto the core surface. The use of 24 K gold is preferred, as this metal is biocompatible and lends a warm, natural color to the final restoration. The equipment has internally programmed processes which automatically checks the temperature and intensity of the current flow. Desired thickness for this application is about 0.2 mm and is generally achieved in about 8–11 hours, using a standard 24 K gold electroplating solution. When deposition is complete, the outer surface is sandblasted and a coating of Bonder A is applied to the gold, and baked by firing at 950° C. for six minutes.

Standard porcelain layering techniques well known in the art are used to complete the restoration of the present invention. Only a thin layer of opaque is necessary because the layer of gold has an ideal warm tone for the finished restoration. After a final contour, stain and glaze, the completed restoration is ready for the dentist to cement or bond to the patient's prepared teeth.

Non-dental applications, such as the creation of jewelry, which require the strength or aesthetic characteristics of the present system are also contemplated. All disclosures of the references described herein are hereby incorporated by reference.

Other variations and modifications of the present invention will be apparent to those of ordinary skill in the art, and it is the intent of the appended claims that such variations and modifications be covered. The particular values and configurations discussed above can be varied, are cited to illustrate particular embodiments of the present invention and are not intended to limit the scope of the invention. It is contemplated that the use of the present invention can involve components having different characteristics as long as the principle, the presentation of a biocompatible dental restoration system using layers of high strength ceramic, gold, and porcelain, is followed.

What is claimed is:

1. A dental restoration method comprising the steps of:
   a. obtaining a prepared bridging ceramic core;
   b. applying a first bonder layer to the core;
   c. baking, for a predetermined time, the first bonder layer upon the core by a means for heating;
   d. providing a stone duplicate which duplicates one or more abutments;
   e. attaching the core to the one or more abutments by a means for attaching;
   f. securely coupling a conductive means to the stone duplicate by a means for coupling;
   g. providing a conductive path which encases the bridging ceramic core and abutments;
   h. electroforming a metal layer upon the bridging ceramic core and the one more abutments to a desired thickness by a means for electroforming resulting in a bridging structure;
   i. applying a second bonder layer to the metal layer;
   j. baking, for a predetermined time, the second bonder layer upon the metal layer by the means for heating; and
   k. baking, for a predetermined time, an outer porcelain layer to the second bonder layer by the means for heating.

2. The dental restoration method of claim 1 further including the step of applying a glaze layer upon the porcelain layer resulting in a glazed structure.

3. The dental restoration method of claim 2 wherein the metal is gold.

4. The dental restoration method of claim 3 wherein the gold is 24 K gold.

5. The dental restoration method of claim 2 wherein the metal is platinum.

6. The dental restoration method of claim 4 wherein the step of obtaining a prepared bridging ceramic core comprises the steps of:
   a. obtaining a master stone cast from a dental impression;
   b. marking margins of the cast resulting in margin lines;
   c. making a silicone impression of the master cast;
   d. casting a plaster cast and a stone cast from the silicone impression;
   e. applying a sealer to the plaster cast;
   f. preparing a slip mixture by admixing a mixing fluid with a binder, placing the mixture into an ultrasonic apparatus and therein sprinkling a $Al_2O_3$-based powder with the mixture resulting in a slip liquid;
   g. placing the slip liquid into a vacuum for a predetermined time;
   h. applying a layer of the liquid slip to the plaster cast;
   i. reducing the layer until the margin lines are visible;
   j. firing the plaster cast at least twice for a known time and temperature;
   k. baking the plaster cast for a known time and temperature resulting in a sintered bridging ceramic core; and
   l. removing the sintered bridging core from the plaster cast, transferring the core to the master cast and adjusting the core with an instrument;
   m. applying a glass-based mixture upon the core and thereafter baking the core for a known time and temperature resulting in a high-strength prepared bridging ceramic core.

7. The dental restoration method of claim 7 wherein the $Al_2O_3$-based powder is a mixture of $Al_2O_3$ and $Al_2O_3$—$ZrO_2$.

8. A multilayer dental restoration system comprising:
   a. a prepared bridging ceramic core having a surface;
   b. a first layer of bonder baked upon the surface by a means for heating;
   c. a stone duplicate which duplicates one or more abutments, the core connecting each abutment;
   d. a biocompatible metal layer electroformed on to the bonder layer and the one or more abutments by a means for electroforming;
   e. a second layer of bonder baked to the metal layer by the means for heating; and
   f. at least one layer of porcelain applied upon the second bonder layer.

9. The system of claim 8 further comprising a glaze layer formed upon the porcelain layer.

10. The system of claim 9 wherein the metal is gold.

11. The system of claim 10 wherein the gold is 24 K gold.

12. The system of claim 9 wherein the metal is platinum.

13. A multilayer dental restoration system comprising:
   a. a prepared bridging ceramic core having a surface, the core prepared by obtaining a master stone cast from a dental impression, marking margins of the cast resulting in margin lines, making a silicone impression of the master cast, casting a plaster cast and a stone cast from the silicon impression, applying a sealer to the plaster cast, preparing a slip mixture by admixing a mixing fluid with a binder, placing the mixture into an ultrasonic apparatus and therein sprinkling a $Al_2O_3$-based powder with the mixture resulting in a slip liquid, placing the slip liquid into a vacuum for a predetermined time, applying a core layer of the liquid slip to the plaster cast, reducing the layer until the margin lines are visible, firing the plaster cast at least once for a known time and temperature, fitting the core to the master cast, glass filtration firing the bridging core and baking the core for a known time and temperature;
   b. a first bonder layer fired upon the surface by a means for heating;
   c. a stone duplicate which duplicates one or more abutments, the core connecting each abutment;
   d. a biocompatible metal layer electroformed on to the bonder layer and each abutment by a means for electroforming;
   e. a second bonder layer fired to the metal layer by the means for heating; and
   f. at least one layer of porcelain applied upon the second bonder layer.

14. The system of claim 13 further comprising a glaze layer formed upon the porcelain layer.

15. The system of claim 13 wherein the $Al_2O_3$-based powder is a mixture of $Al_2O_3$ and $Al_2O_3$—$ZrO_2$.

16. The system of claim 17 wherein the metal is gold.

17. The system of claim 18 wherein the gold is 24 K gold.

18. The system of claim 17 wherein the metal is platinum.

* * * * *